(12) United States Patent
Herr

(10) Patent No.: US 9,084,689 B2
(45) Date of Patent: Jul. 21, 2015

(54) VARIABLE-MECHANICAL-IMPEDANCE ARTIFICIAL LEGS

(71) Applicant: IWALK, INC., Bedford, MA (US)

(72) Inventor: Hugh Miller Herr, Somerville, MA (US)

(73) Assignee: IWALK, INC., Bedford, MA (US)

( * ) Notice: Subject to any disclaimer, the term of this patent is extended or adjusted under 35 U.S.C. 154(b) by 0 days.

(21) Appl. No.: 14/090,556

(22) Filed: Nov. 26, 2013

(65) Prior Publication Data

US 2014/0088728 A1 Mar. 27, 2014

Related U.S. Application Data

(63) Continuation of application No. 10/613,499, filed on Jul. 3, 2003, now abandoned.

(60) Provisional application No. 60/395,938, filed on Jul. 15, 2002.

(51) Int. Cl.
| | |
|---|---|
| *A61F 2/64* | (2006.01) |
| *A61F 2/60* | (2006.01) |
| *A61F 2/66* | (2006.01) |
| *A61F 2/68* | (2006.01) |
| *A61F 5/01* | (2006.01) |
| *A61F 2/50* | (2006.01) |

(52) U.S. Cl.
CPC ... *A61F 2/60* (2013.01); *A61F 2/66* (2013.01); *A61F 5/01* (2013.01); *A61F 2/6607* (2013.01); *A61F 2002/503* (2013.01); *A61F 2002/5007* (2013.01); *A61F 2002/5033* (2013.01); *A61F 2002/6621* (2013.01); *A61F 2002/6845* (2013.01); *A61F 2005/0134* (2013.01); *A61F 2005/0169* (2013.01)

(58) Field of Classification Search
CPC ............... A61F 2/60; A61F 2002/503; A61F 2002/5033; A61F 2002/6845
USPC ........................ 623/24, 26, 27, 40, 42, 44, 46
See application file for complete search history.

(56) References Cited

U.S. PATENT DOCUMENTS

| | | | | | |
|---|---|---|---|---|---|
| 45,169 | A | * | 11/1864 | Neubert | 623/42 |
| 595,634 | A | * | 12/1897 | King | 623/42 |
| 3,546,712 | A | * | 12/1970 | Tarte | 623/41 |

* cited by examiner

*Primary Examiner* — David H Willse
*Assistant Examiner* — Javier Blanco
(74) *Attorney, Agent, or Firm* — Kacvinsky Daisak Bluni PLLC

(57) ABSTRACT

In one aspect, the invention provides methods and apparatus facilitating an adjustable-stiffness prosthesis or orthosis (including approximations to arbitrarily definable non-linear spring functions). Spring rates may be varied under no-load conditions during a walking gate cycle to minimize power consumption. In another aspect, the invention provides methods and apparatus for outputting positive power from a prosthesis or orthosis, facilitating high-performance artificial limbs. In one embodiment of the invention, the positive power is transferred from a functioning muscle to the prosthesis or orthosis, which mimics or assists a non-functioning or impaired muscle. In another embodiment of the invention, the positive power comes from an on-board power source in the prosthesis or orthosis.

19 Claims, 15 Drawing Sheets

External, Bi-articular Transfemoral Prosthesis, Robotic Limb, or Orthotic Brace in Heel-Strike to Toe-Off Walking Sequence External Prosthesis, Robotic Limb, or Orthothosis in Heel Strike to Toe-Off Walking Sequence Prosthetic Mechanisms Designed to Power Plantar-flex Catapult Leg Prosthesis for Walking, Running, and Jumping Catapult Leg Prosthesis for Walking, Running, and Jumping External, Bi-articular Transfemoral Prosthesis, Robotic Limb, or Orthotic Brace in Heel-Strike to Toe-Off Walking Sequence External, Bi-articular/Ttransfemoral Prosthesis in Heel-Strike to Toe-Off Walking Sequence Variable Spring-Rate Joint Low-Profile Prosthetic Foot Example Prosthetic Ankle/Foot Variable-Spring-Rate Multiple-Pneumatic-Chamber and Energy Transfer System.

Prosthetic Ankle-Foot

Prior-Art Prosthetic Ankle-Foot

Variable Stiffness Spring for an External Prosthesis

VARIABLE-MECHANICAL-IMPEDANCE ARTIFICIAL LEGS

This patent application is a continuation of U.S. patent application No. 10/613,499 filed Jul. 3, 2003, entitled "Variable-Mechanical-Impedance Artificial Legs"(now abandoned) which claims priority to and the benefit of U.S. Provisional Patent Application No. 60/395,938, filed Jul. 15, 2002, entitled "Variable-Mechanical-Impedance Artificial Legs"the entire contents of each of which is hereby incorporated by reference in their entirety.

The invention relates generally to the fields of legged robotics, orthotic leg devices and prosthetic leg joints, and more specifically to artificial limbs with time-variable mechanical parameters.

BACKGROUND

Prosthetic limbs have come a long way since the days of simple wooden "peg legs". Today, amputee men running on a prosthetic leg can beat race times of the best unimpaired women runners. It is believed that new advances in prosthetic limbs (such as those embodied in the present invention) will soon lead to amputees being able to out-perform the best unimpaired athletes of the same sex in sports such as running. It is an object of the present invention to advance the state of prosthetic limbs to a new level, providing increased athletic performance, increased control, and reduced body strain. It is a further object of the present invention to provide essential elements needed for making prosthetic limbs that more accurately mimic the mechanical behavior of healthy human limbs.

Description of Normal, Level-Ground Walking:

In order to establish terminology used in this document, the basic walking progression from heel strike to toe off is first explained. There are three distinct phases to a walking stance-period as depicted in FIG. 1 with heel-toe sequence 1 through 7.

Saggital Plane Knee Phases
1. Beginning with heel strike, the stance knee begins to flex slightly (Sequence 1-3). This flexion allows for shock absorption upon impact as well as keeping the body's center of gravity at a more constant vertical level throughout stance.
2. After maximum flexion is reached in the stance knee, the joint begins to extend again, until full extension is reached (Sequence 3-5).
3. During late stance, the knee of the supporting leg begins to flex again in preparation for the swing phase (Sequence 5-7). This is referred to in the literature as "knee break". At this time, the adjacent foot strikes the ground and the body is in "double support mode" (that is to say, both legs are supporting body weight).

Saggital Plane Ankle Phases
1. Beginning with heel strike, the ankle undergoes a controlled plantar-flexion phase where the foot rotates towards the ground until the forefoot makes contact (Sequence 1-2).
2. After controlled plantar-flexion, the ankle undergoes a controlled dorsi-flexion phase where the tibia rotates forwardly while the foot remains in contact with the ground (Sequence 2-5).
3. During late stance, the ankle undergoes a powered plantar-flexion phase where the forefoot presses against the ground raising the heel from the ground (Sequence 5-7). This final phase of walking delivers a maximal level of mechanical power to the walking step to slow the fall of the body prior to heel strike of the adjacent, forwardly positioned leg.

The development of artificial leg systems that exhibit natural knee and ankle movements has been a long standing goal for designers of legged robots, prostheses and orthoses. In recent years, significant progress has been made in this area. The current state-of-the-art in prosthetic knee technology, the Otto Bock C-Leg, enables amputees to walk with early stance knee flexion and extension, and the state-of-the-art in ankle-foot systems (such as the Össur Flex-Foot) allow for ankle controlled plantar-flexion and dorsi-flexion. Although these systems restore a high level of functionality to leg amputees, they nonetheless fail to restore normal levels of ankle powered plantar-flexion, a movement considered important not only for biological realism but also for walking economy. In FIG. 2, ankle power data are shown for ten normal subjects walking at four walking speeds from slow (½ m/sec) to fast (1.8 m/sec). As walking speed increases, both positive mechanical work and peak mechanical power output increase dramatically. Many ankle-foot systems, most notably the Flex-Foot, employ springs that store and release energy during each walking step. Although some power plantar-flexion is possible with these elastic systems, normal biological levels are not possible. In addition to power limitations, the flex-foot also does not change stiffness in response to disturbances. The human ankle-foot system has been observed to change stiffness in response to forward speed variation and ground irregularities. In FIG. 3, data are shown for a normal subject walking at three speeds, showing that as speed increases ankle stiffness during controlled plantar-flexion increases.

Artificial legs with a mechanical impedance that can be modeled as a spring in parallel with a damper are known in the art. Some prostheses with non-linear spring rates or variable damping rates are also known in the art. Unfortunately, any simple linear or non-linear spring action cannot adequately mimic a natural limb that puts out positive power during part of the gait cycle. A simple non-linear spring function is monotonic, and the force vs. displacement function is the same while loading the spring as while unloading the spring. It is an object of the present invention to provide actively electronically controlled prosthetic limbs which improve significantly on the performance of artificial legs known in the art, and which require minimal power from batteries and the like. It is a further object of the present invention to provide advanced electronically-controlled artificial legs which still function reasonably well should the active control function fail (for instance due to power to the electronics of the limb being lost). Still further, it is an object of the present invention to provide artificial legs capable of delivering power at places in the gait cycle where a normal biological ankle delivers power. And finally, it is an object of the present invention to provide prosthetic legs with a controlled mechanical impedance and the ability to deliver power, while minimizing the inertial moment of the limb about the point where it attaches to the residual biological limb.

During use, biological limbs can be modeled as a variable spring-rate spring in parallel with a variable damping-rate damper in parallel with a variable-power-output forcing function (as shown in FIG. 4a). In some activities, natural human limbs act mostly as spring-damper combinations. One example of such an activity is a slow walk. When walking slowly, a person's lower legs (foot and ankle system) act mostly as a system of springs and dampers. As walking speed increases, the energy-per-step put out by the muscles in the lower leg increases. This is supported by the data in FIG. 2.

Muscle tissue can be controlled through nerve impulses to provide variable spring rate, variable damping rate, and variable forcing function. It is an objective of the present invention to better emulate the wide range of controllability of damping rate, spring rate, and forcing function provided by human muscles, and in some cases to provide combination of these functions which are outside the range of natural muscles.

SUMMARY OF THE INVENTION

There are two major classes of embodiments of the present invention. The first major class provides for actively controlled passive mechanical parameters (actively controlled spring rate and damping rate). This major class of embodiments will be referred to as variable-stiffness embodiments. Three sub-classes of variable-stiffness embodiments are disclosed:
 1) Multiple parallel interlockable springs.
 2) Variable mechanical advantage.
 3) Pressure-variable pneumatics.

The second major class of embodiments of the present invention allows for the controlled storage and release of mechanical energy within a gait cycle according to any arbitrary function, including functions not available through simple nonlinear springs. Within this second major class of embodiments, energy can be stored and released at rates which are variable under active control. Thus for a given joint, the force vs. displacement function is not constrained to be monotonic or single-valued. Within this class of embodiments, energy (from either muscle or a separate on-board power source) can be stored and released along arbitrarily defined functions of joint angular or linear displacement, force, etc. This major subclass of embodiments shall be referred to herein as energy transfer embodiments. Two subclasses of energy transfer embodiments are disclosed:
 1) Bi-articular embodiments (which transfer energy from a proximal joint to a distal joint to mimic the presence of a missing joint).
 2) Catapult embodiments (which store energy from a power source over one span of time and release it over another span of time to aid locomotion).

The present invention makes possible prostheses that have mechanical impedance components (damping and spring rate) and power output components that are actively controllable as functions of joint position, angular velocity, and phase of gait. When used in a prosthetic leg, the present invention makes possible control of mechanical parameters as a function of how fast the user is walking or running, and as a function of where within a particular step the prosthetic leg is operating.

It is often necessary to apply positive mechanical power in running shoes or in orthotic and prosthetic (O&P) leg joints to increase locomotory speed, to jump higher, or to produce a more natural walking or running gait. For example, when walking at moderate to high speeds, the ankle generates mechanical power to propel the lower leg upwards and forwards during swing phase initiation. In FIG. 2, data are shown for ten normal subjects showing that the ankle delivers more energy during a single step than it absorbs, especially for moderate to fast walking speeds.

Two catapult embodiments of the present invention are described in which elastic strain energy is stored during a walking, running or jumping phase and later used to power joint movements. In a first embodiment, catapult systems are described in which storage and release of stored elastic energy occurs without delay. In a second embodiment, elastic strain energy is stored and held for some time period before release. In each Embodiment, mechanism architecture, sensing and control systems are described for shoe and O&P leg devices. Although just a few devices are described herein, it is to be understood that the principles could be used for a wide variety of applications within the fields of human-machine systems or legged robots. Examples of these first and second catapult embodiments are shown in FIGS. 4 through 6.

One bi-articular embodiment of the invention described herein comprises a system of knee-ankle springs and clutches that afford a transfer of energy from hip muscle extensor work to artificial ankle work to power late stance plantar-flexion. Since the energy for ankle plantar-flexion originates from muscle activity about the hip, a motor and power supply need not be placed at the ankle, lowering the total mass of the knee-ankle prosthesis and consequently the metabolic cost associated with accelerating the legs in walking. Examples of these embodiments are shown in FIGS. 7 and 8.

Several variable-stiffness embodiments are described herein in which variable spring-rate structures are constructed by varying the length of a moment arm which attaches to a spring element about a pivot axis, thus providing a variable rotational spring rate about the pivot axis. Examples of such embodiments are depicted in FIGS. 9 through 11. In a preferred embodiment, variations in the length of the moment arm are made under microprocessor control at times of zero load, to minimize power consumed in the active control system.

Variable-stiffness embodiments of the present invention employing multiple interlockable parallel spring elements are depicted in FIGS. 12 through 14. In FIGS. 12a and 12b, multiple parallel elastic leaf spring elements undergo paired interlocking at pre-set joint flexures or under microprocessor control. This embodiment makes possible arbitrary piecewise-linear approximations to non-linear spring functions (such as function 624 in FIG. 12d). A pneumatic embodiment which can be configured to behave similarly to the leaf spring embodiments shown in FIGS. 12a and 12b is shown in FIG. 13. In the pneumatic embodiment of FIG. 13, valves are electronically closed to effectively increase the number of pneumatic springs in parallel.

The multiple parallel spring elements in FIGS. 12a, 12b, and FIG. 13 could equivalently be replaced by other types of spring elements, such as coil springs, torsion bars, elastomeric blocks, etc.

DETAILED DESCRIPTION

Figure 1:
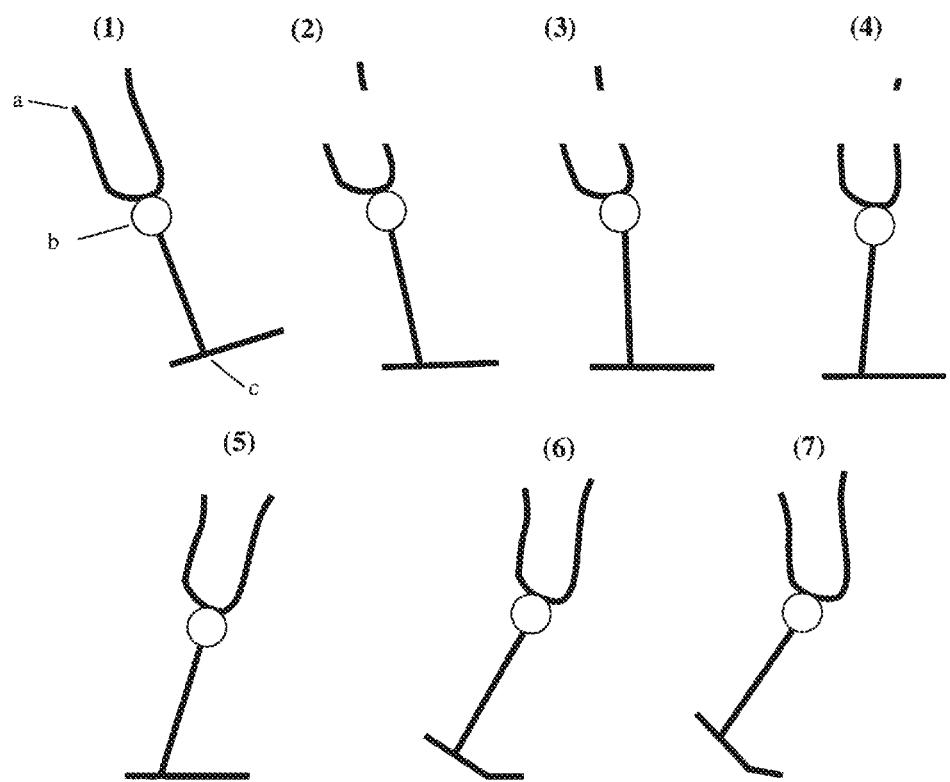
FIG. 1: Depiction of stages of a gait cycle, including controlled plantar-flexion, controlled dorsi-flexion, and powered plantar-flexion.
Figure 2:
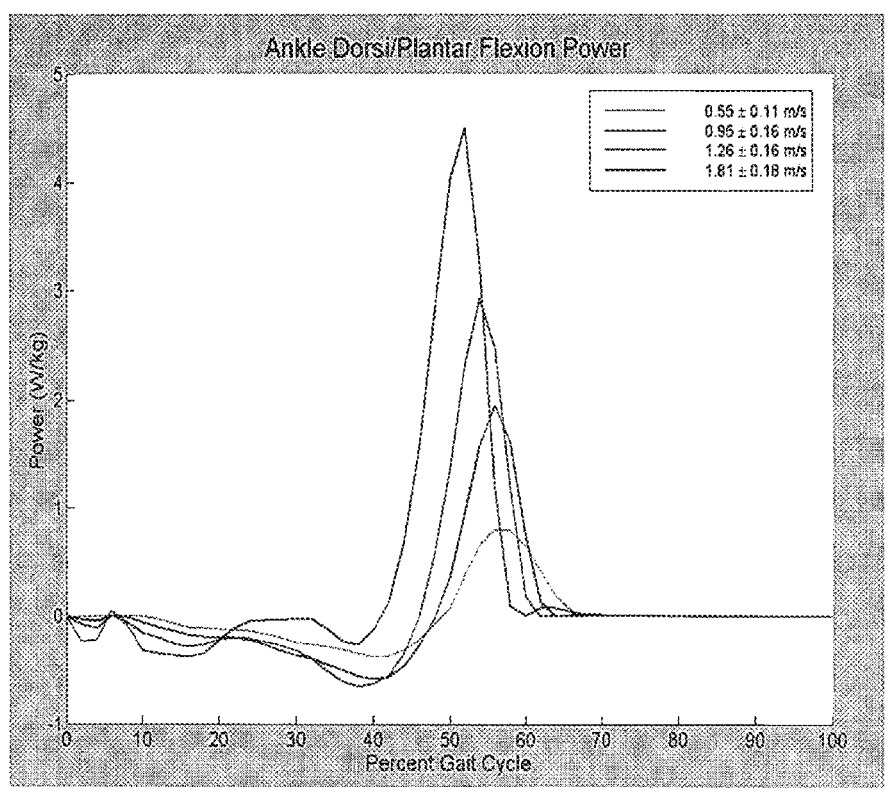
FIG. 2: Data from ten normal subjects are plotted showing mechanical power output versus percent gait cycle in walking. Both zero and one hundred percent gait cycle correspond to heel strike of the same foot
Figure 3:
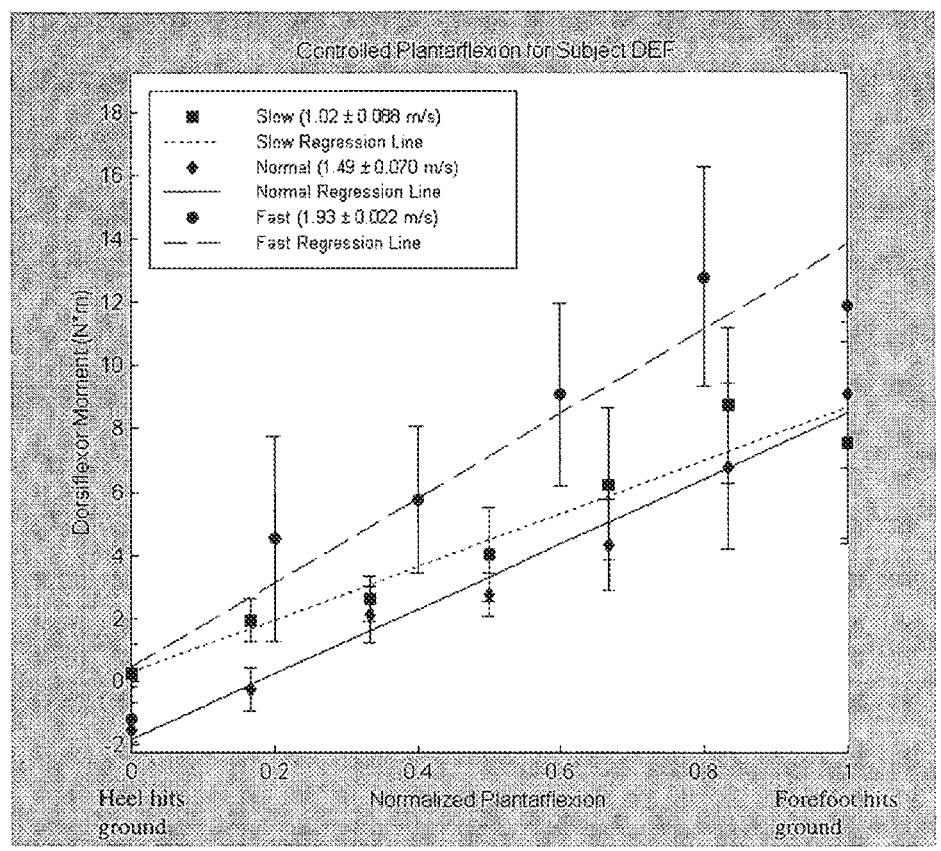
FIG. 3: Data for one subject, showing normal biological ankle function during the controlled plantar-flexion phase of walking.

A powered-catapult embodiment of the present invention is shown in FIGS. 4a-4d. FIG. 4a is a lumped-element model of a powered-catapult prosthetic. The mounted end 203 of the prosthesis attaches to the body, and the distal end 204 of the prosthesis interfaces to the environment (such as the ground for a leg prosthesis). Mounted end 203 is coupled to distal end 204 through spring 202, and through the series combination of force actuator 205 and force sensor 201. In some embodiments, displacement sensor 206 may also be included in parallel with spring 202. If the system is designed to operate in parallel with an existing limb, the muscles of the existing limb are modeled by muscle 200.

A mechanical implementation of lumped-element diagram 4a is shown in side view in FIG. 4c and in front view in FIG. 4d. In a preferred embodiment, during the portion of a gait cycle when the foot is not in contact with the ground, motor 205 turns spool 209 to wind on some of tension band 208, storing energy in spring 202. Force sensor 201 and winding distance sensor 207 may be used in a control loop to control how much energy is stored in spring 202, and how rapidly this energy is stored. Once the desired energy has been stored, clutch 207 is actuated to keep tension band 208 from unwinding and spring 202 from relaxing until the control system decides to release the stored energy. The energy stored in spring 202 during the swing phase of the gait cycle is represented by the dark area on the force vs. distance graph shown in FIG. 4b.

During the powered plantar-flexion phase of the gait cycle, the control system releases clutch 207, allowing the stored energy in spring 202 to be released, imitating the powered plantar-flexion stage of a normal gait cycle. This release of energy mimics the pulse of power put out by a biological ankle during the powered plantar-flexion stage of a walking or running gait cycle.

In an alternate embodiment, motor 205 may store energy in spring 202 at the same time as the natural leg stores impact energy during the gait cycle. This embodiment can be used to effectively implement one spring rate during compression (such as the spring rate depicted by the line from the origin to point Kd in FIG. 4b) and another spring rate during release (such as the spring rate depicted by the line from the origin to point Ks in FIG. 4b).

Figure 4:
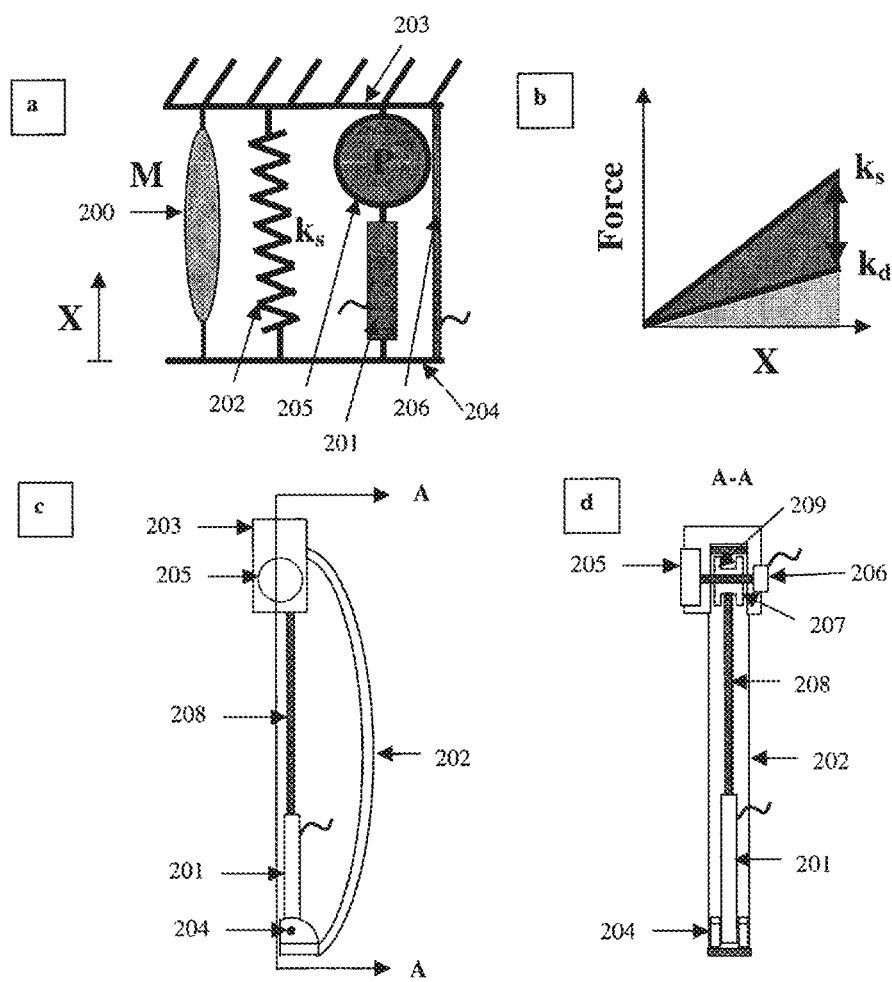
FIG. 4a: Basic catapult embodiment of the present invention, represented in terms of a lumped-parameter model.
FIG. 4b: Force-displacement graph where darkened area represents extra stored energy (used in walking/running) put into catapult system by force actuator while prosthetic foot is off the ground.
FIG. 4c: Side view of simplified prosthetic mechanism designed to provide powered plantar-flexion.
FIG. 4d: Front view of simplified prosthetic mechanism designed to provide powered plantar-flexion.
Figure 5:
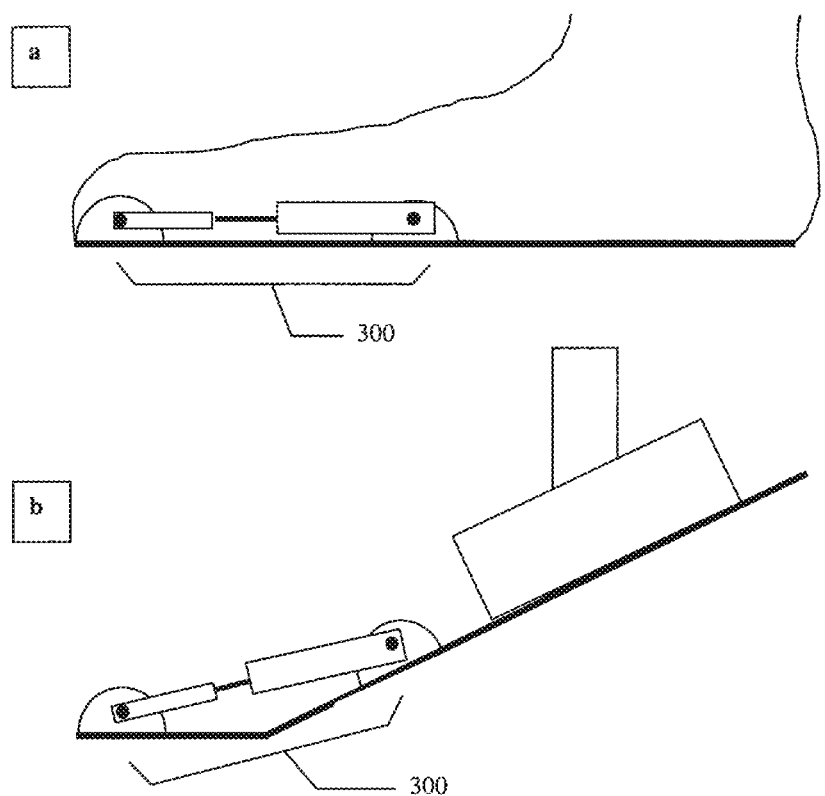
FIG. 5a: Catapult foot prosthesis or shoe orthosis for walking, running, and jumping, shown in the equilibrium configuration.
FIG. 5b: Catapult foot prosthesis or shoe orthosis for walking, running, and jumping, shown in a compressed state.

In an alternate embodiment, FIG. 5 shows a prosthetic foot or shoe orthosis that stores both muscle energy and motor energy in spring mechanism 300 during the gait cycle, for release during the powered plantar-flexion stage of the walking gait cycle (toe-off propulsion). When walking on this type of catapult prosthesis or foot orthosis, a person would experience a first (lower) spring rate (depicted by the line from the origin to point Kd in FIG. 4b), and a second (higher) spring rate (depicted by the line from the origin to point Ks in FIG. 4b) when releasing energy from spring 300 during the powered plantar-flexion phase of the gait cycle.

For catapult embodiments depicted in both FIG. 4 and in FIG. 5, part of the energy released during powered plantar-flexion came from leg muscle action compressing springs 202 and 300, and part came from an electromechanical actuator such as a motor. In a preferred embodiment of the present invention as depicted in FIG. 4, the majority of power stored in spring mechanisms by electromechanical actuators occurs during the minimal-load portion of the walking/running gait cycle (swing phase), and the start of the energy-release phase (late stance phase) of the gait cycle may be time-delayed with respect to the swing phase when motor energy is stored.

Figure 6:
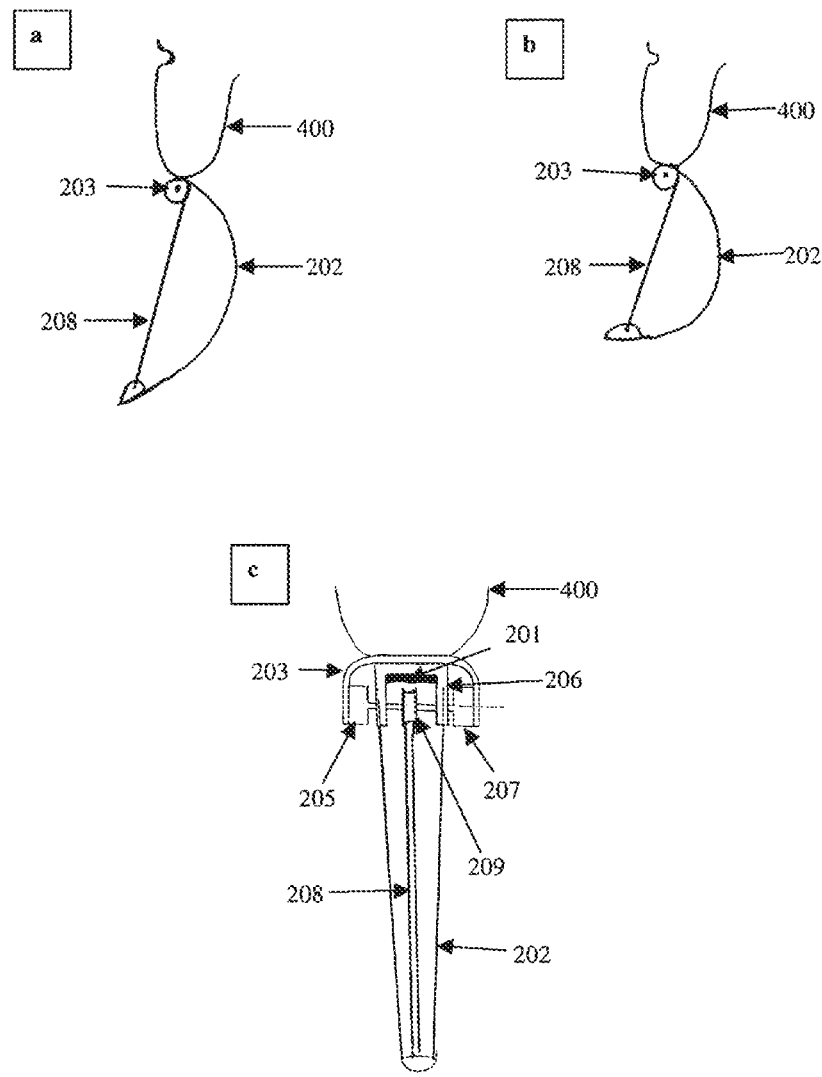
FIG. 6a: Side view of catapult leg prosthesis for walking, running, and jumping, shown in the equilibrium state.
FIG. 6b: Side view of catapult leg prosthesis for walking, running, and jumping, shown in a compressed state.
FIG. 6c: Front view of catapult leg prosthesis for walking, running, and jumping.

FIG. 6 is another depiction of the catapult leg prosthesis of FIG. 4, also showing socket 400, which attaches to the residual biological limb. Although the leg prostheses shown in FIGS. 4 and 6 are below-the-knee prostheses, the invention could also be employed in above-knee prostheses.

Figure 7:
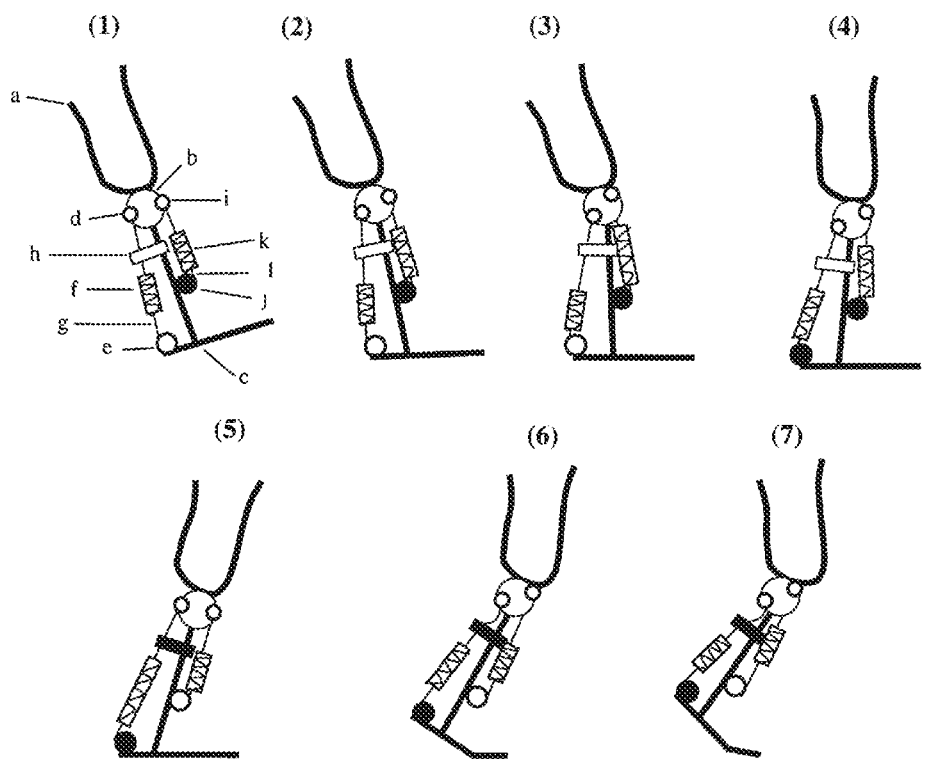
FIG. 7: An external, bi-articular transfemoral prosthesis or orthosis is shown in a heel strike to toe-off walking sequence. The system comprises springs and controllable clutches to transfer energy from hip muscular work to ankle powered plantar-flexion work.
Figure 8:
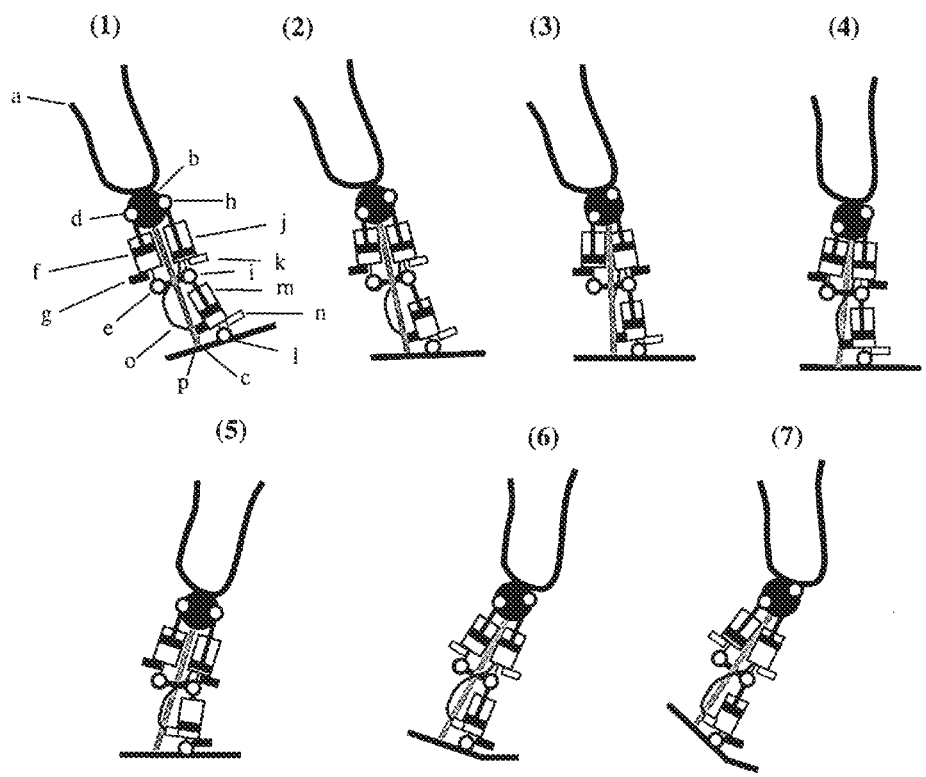
FIG. 8: An external, bi-articular transfemoral prosthesis or orthosis is shown in a heel strike to toe-off walking sequence. The system comprises pneumatic springs and controllable valves to transfer energy from hip muscular work to ankle powered plantar-flexion work.

Two bi-articular embodiments of the present invention are shown in FIGS. 7 and 8. In a first embodiment (FIG. 7), a prosthesis (above or below knee), robotic leg or full leg orthosis is shown having above-knee segment (a), knee joint (b), ankle joint (c), posterior knee pivot (d), posterior clutch (e), posterior spring (f), posterior cord (g), knee-ankle transfer clutch (h), anterior pivot (i), anterior clutch (j), anterior spring (k), and anterior cord (l). Anterior spring (k) stretches and stores energy during early stance knee flexion (from 1 to 3) and then releases that energy during early stance knee extension (from 3 to 5). Here spring (k) exerts zero force when the knee is fully extended, and anterior clutch (j) is engaged or locked throughout early stance knee flexion and extension (from 1 to 5). This stored energy, together with an applied extensor hip moment from either a robotic or biological hip, result in an extensor moment at the knee, forcing the knee to extend and stretching posterior spring (f) (from 3 to 5). The spring equilibrium length of posterior spring (f) is equal to the minimum distance from posterior knee pivot (d) to posterior clutch (e) (leg configuration 3 in FIG. 7). To achieve this spring equilibrium, posterior clutch (e) retracts posterior cord (g) as the distance from posterior knee pivot (d) to posterior clutch (e) becomes smaller. When this distance begins to increase in response to knee extension and ankle dorsi-flexion (from 4 to 5), posterior clutch (e) engages, causing posterior spring (f) to stretch. When the ankle is maximally dorsi-flexed and the knee fully extended (leg configuration 5), posterior spring (f) becomes maximally stretched. When the leg assumes this posture, knee-ankle transfer clutch changes from a disengaged state to an engaged state. Engaging the knee-ankle clutch mechanically grounds spring (f) below the knee rotational axis, and consequently, all the energy stored in spring (f) is transferred through the ankle to power ankle plantar-flexion (from 6 to 7). During late stance (from 5 to 6), the knee of the supporting leg begins to flex again in preparation for the swing phase. For this late stance knee flexion, anterior clutch (j) is disengaged to allow the knee to freely flex without stretching anterior spring (k).

It should be understood that the bi-articular knee-ankle invention of embodiment I (FIG. 7) could assume many variations as would be obvious to those of ordinary skill in the art. For example, the system described herein could act in parallel to additional ankle-foot springs and/or to an active or passive knee damper. Additionally, instead of mechanically grounding spring (f) distal to the knee axis to effectively transfer all the stored energy through the ankle, the perpendicular distance from the line of spring force (f) to the knee's axis of rotation could go to zero as the knee approaches full extension.

In a second embodiment (FIG. 8), a prosthesis (above or below knee), robotic leg or full leg orthosis is shown having a similar energy transfer from hip muscle extensors to artificial leg to power ankle plantar-flexion, accept energies are stored within pneumatic springs about the knee and then transferred to the ankle via a fluid transfer system. In this embodiment, the transfer of energy occurs without a physical bi-articular spring such as posterior spring (f) in FIG. 7. In this embodiment, anterior pneumatic spring (j) compresses and stores energy during early stance knee flexion (from 1 to 3). Here anterior knee valve (k) is closed or locked throughout early stance knee flexion and extension (from 1 to 5). This stored energy, together with an applied extensor hip moment from either a robotic or biological hip, result in an extensor moment at the knee, forcing the knee to extend and compress posterior pneumatic spring (f) (from 3 to 5). It is important to note that posterior knee valve (g) is open during early stance knee flexion so that posterior pneumatic spring (f) exerts little force. Knee valve (g) is then closed during knee extension so that energy is stored in the posterior pneumatic spring (f). When the ankle is maximally dorsi-flexed and the knee fully extended (leg configuration 5), posterior pneumatic spring (f) is maximally compressed. When the leg assumes this posture, knee-ankle transfer valve changes from a closed state to an open state, and anterior ankle valve (n) changes to a closed state, allowing all the energy stored in spring (f) is be transferred through the ankle to power ankle plantar-flexion (from 6 to 7). During late stance (from 5 to 6), the knee of the supporting leg begins to flex again in preparation for the swing phase. For this late stance knee flexion, anterior and posterior valves (g, k) are open to allow the knee to freely flex without compressing anterior spring (j).

It should be understood that the bi-articular knee-ankle invention of embodiment II (FIG. 8) could assume many variations as would be obvious to those of ordinary skill in the art. For example, the system described herein could act in parallel to active or passive ankle-foot springs and/or to an active or passive knee damper. Additionally, the energy in posterior pneumatic spring (f) could be transferred to a temporary holding chamber to be later released to the ankle during powered plantar-flexion.

Figure 9:
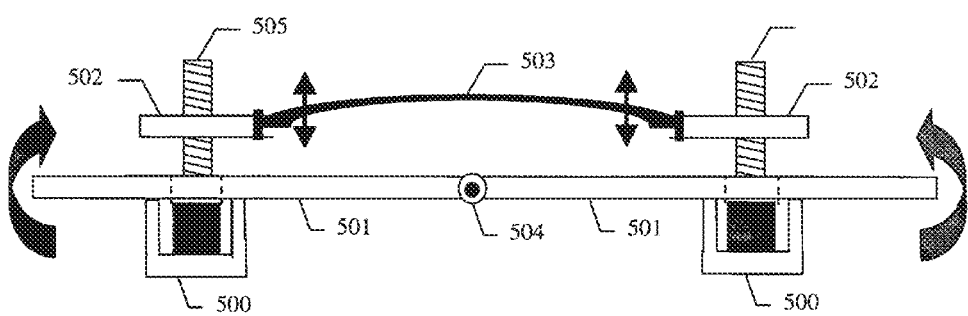
FIG. 9: Perpendicularly-variable-moment pivotal spring structure.

The mechanical system in FIG. 9 is a variable-mechanical-advantage embodiment of a variable-stiffness spring. Motors 500 and motor-driven screws 505 serve to change the moment of compression of bow spring 503 about pivot point 504. This mechanism may be used to adjust spring stiffness with minimal power under no-load conditions. It may also be used as an alternative way of storing energy in a spring which is under load, and thus may be used as a component of an immediate-release catapult system such as depicted in FIG. 5.

Figure 10:
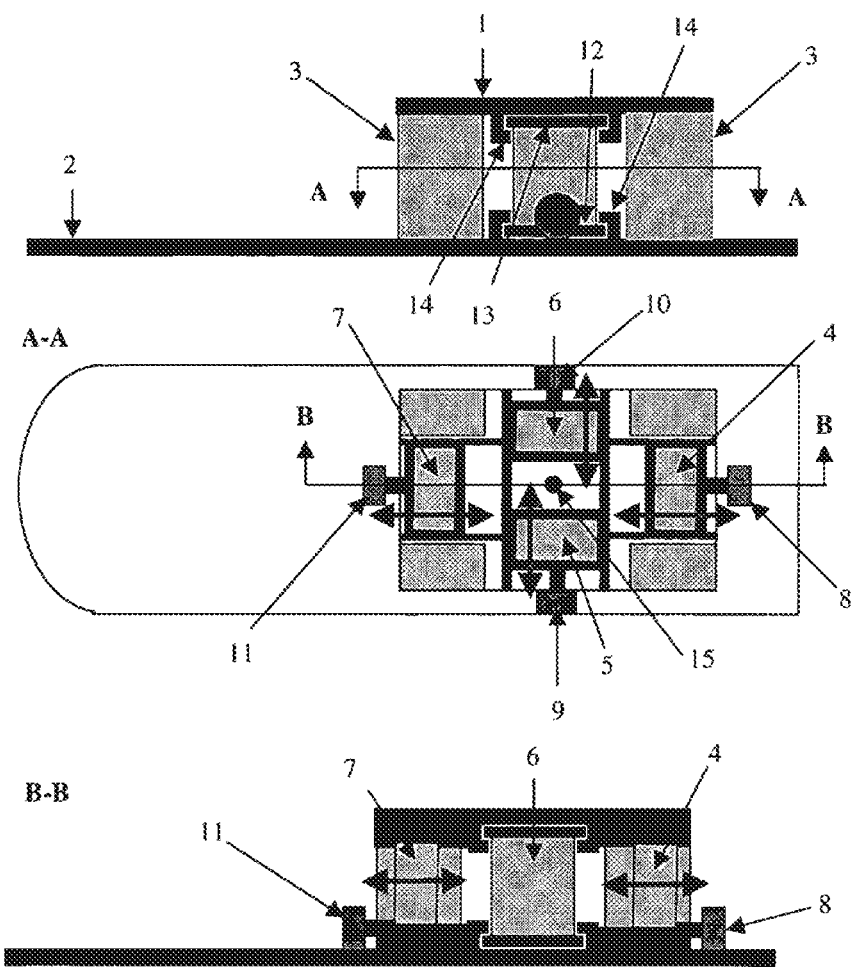
FIG. 10: Mechanical diagram of a low-profile prosthetic foot where spring elements are actively controlled (positioned) to affect ankle joint stiffness.

FIG. 10 depicts a low-profile prosthetic foot-ankle with top plate 1 and bottom plate 2, where spring elements are actively controlled (positioned) to affect ankle joint stiffness. This embodiment of the present invention is a variable-stiffness embodiment of the "variable mechanical advantage" sub-class. In this low-profile prosthetic ankle joint embodiment, side-to-side spring rates of the prosthetic ankle and front-to-back spring rates of the prosthetic ankle are adjusted by varying the distance of spring elements 4, 5, 6, and 7 from the central pivot point 15 of the ankle joint. Spring top plates 13 and spring bottom plates 12 of spring elements 4, 5, 6, and 7 slide in tracks 14, driven by position-adjusting motors 8, 9, 10, and 11. In a preferred embodiment, motors 8, 9, 10, and 11 only change the positions of spring elements 4, 5, 6, and 7 when the ankle joint is under zero load (for instance, during the part of the walking gait when the foot is not in contact with the ground). Adjustment of spring position under zero load allows position adjustments to be done with minimal energy. This embodiment offers independent inversion/eversion stiffness control as well as independent plantar-flexion and dorsi-flexion control.

Figure 11:
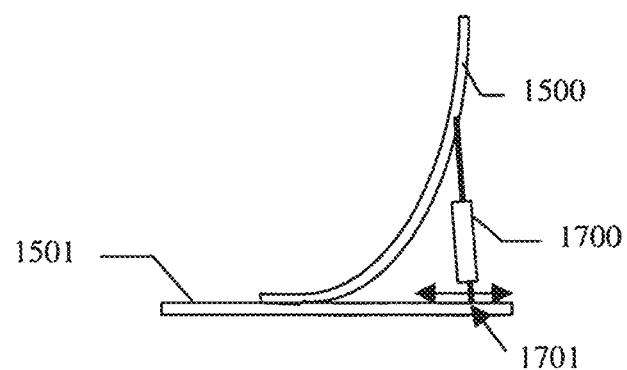
FIG. 11: Variable-stiffness joint according to the present invention, utilizing variable mechanical advantage to produce variable spring rate and/or variable damping rate.

A variable stiffness ankle-foot prosthesis embodiment according to the present invention is shown in FIG. 11. Constant-rate spring or damping element 1700 fixedly attached at one end and movably attached at the other end. Attachment point 1701 may be moved in and out with respect to the effective pivot point of the ankle joint. If element 1700 is a damping element, this configuration provides a variable damping ankle joint. If element 1700 is a spring element, this configuration provides a variable spring rate ankle joint. FIGS. 9, 10 and 11 demonstrate how a constant element can be transformed into a variable element according to the present invention, by varying mechanical advantage. In non-catapult preferred embodiments of the present invention, the variation in mechanical advantage takes place such that the motion used to vary the mechanical advantage takes place substantially perpendicular to the force the element being moved is under, thus minimizing the work needed to vary the mechanical advantage.

Figure 12:
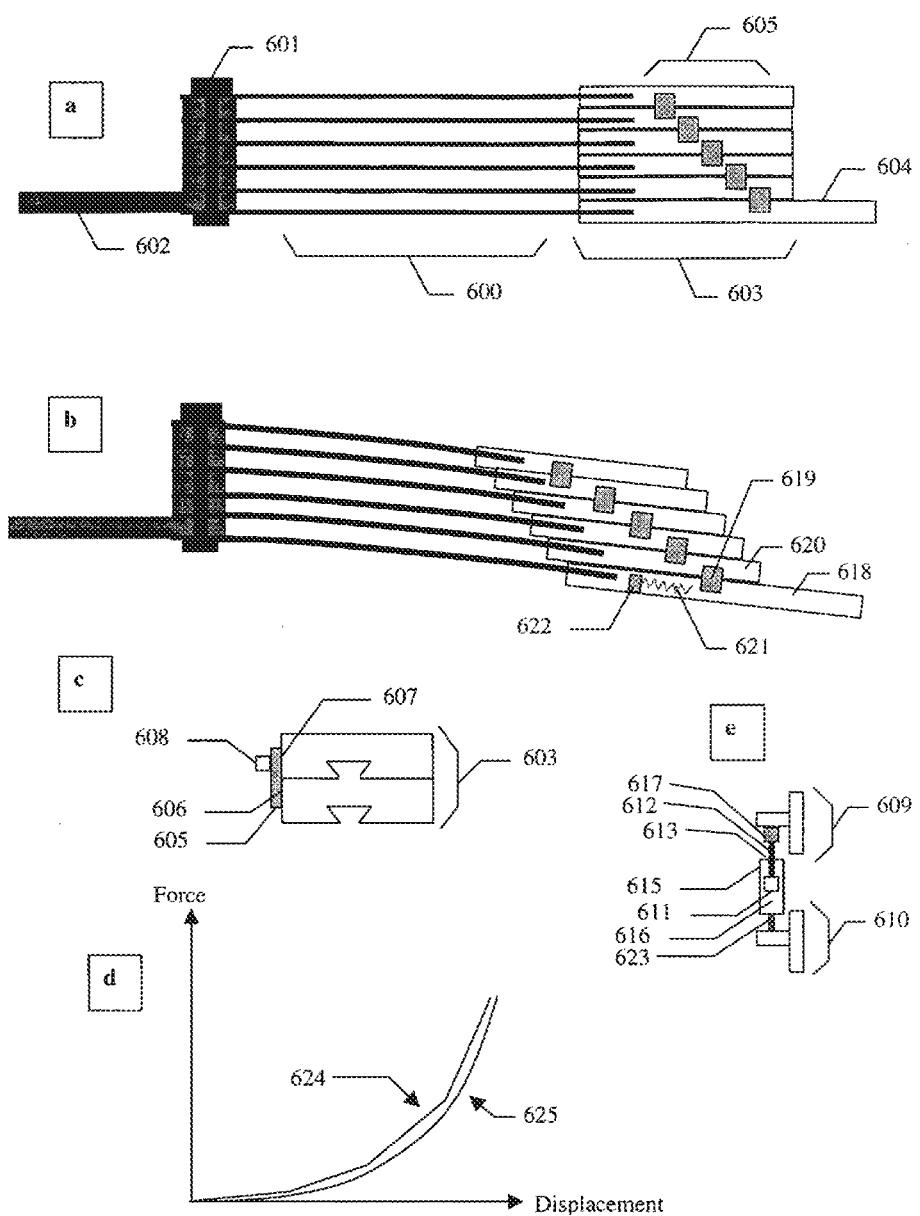
FIG. 12a: Multiply interlockable parallel leaf spring structure, shown in equilibrium position.
FIG. 12b: Multiply interlockable parallel leaf spring structure, shown in a stored-energy position.
FIG. 12c: End view of two dove-tailed slidably attached leaf spring terminations with controllable interlock actuator.
FIG. 12d: Piecewise-linear approximation to nonlinear spring function achieved by interlocking successive parallel leaf springs at various angles, and smoothed nonlinear spring function achieved by interlocking successive parallel leaf springs through coupling springs.
FIG. 12e: Nonlinear damping element coupling mechanism for coupling multiple spring elements.

FIGS. 12a and 12b depict a multiple-parallel-leaf-spring embodiment of a variable mechanical impedance according to the present invention. Leaf springs 600 are bound together and bound tightly to attaching bracket 602 at one end by bolt 601. At the other end, leaf springs terminate in slidably interlocking blocks 603, which may be locked together dynamically in pairs by interlocking plates 605. Each interlocking plate 605 is permanently bonded to one leaf spring terminator block 603 at surface interface 606, and controllably bindable to a second leaf spring terminator block 604 at a second interface 607, by binding actuator 608. Binding actuator 608 may bind surface interface 607 by any number of means such as mechanical clamp, pin-in-socket, magnetic clamp, etc. Adjacent leaf spring terminator blocks are slidably attached by dovetail slides or the like. The structure shown in FIGS. 12a-c can be used to implement a piecewise-linear spring function such as function 604 depicted in FIG. 12d, by engaging successive interlocks 605 at pre-determined points in spring flexure, and disengaging at like points.

In a preferred embodiment, the slope discontinuities in function 604 may be "smoothed" by coupling successive leaf springs through coupling springs. In FIG. 12d, stop plate 619 is affixed to leaf spring termination 620, and coupling spring 621 is mounted to leaf spring termination 618 through coupling spring mount 622. Leaf spring termination 620 is free to slide with respect to leaf spring termination 618 until coupling spring 621 and stop plate 619 come in contact. Coupling spring 621 acts to smooth the transition from the uncoupled stiffness of two leaf springs to the coupled stiffness of two leaf springs, resulting in smoothed force-displacement function 625 in FIG. 12d.

In a preferred embodiment, coupling spring 621 is itself a stiff, nonlinear spring. In another preferred embodiment, coupling spring 621 may have actively controllable stiffness, and may be made according to any of variable-stiffness spring embodiments of the present invention.

FIG. 12e depicts a non-linear dissipative coupling mechanism for coupling pairs of spring elements in a multiple-parallel-element spring. Mechanical mounts 609 and 610 affix to a pair of spring elements to be coupled. In a preferred embodiment, one of 609 and 610 is permanently affixed and the other of 609 and 610 is controllably affixed through a mechanism such as 608 described above. Piston 611 is coupled to mount 609 through rod 612 which passes through seal 614. Thus piston 611 may move back and forth in chamber 615 along the axis of rod 612. Chamber 615 is preferably filled with viscose or thixotropic substance 616. A viscose substance can be used in chamber 616 to provide a mechanical coupling force proportional to the square of the differential velocity between mounts 609 and 610. A thixotropic substance (such as a mixture of corn starch and water) can be used to provide an even more nonlinear relationship between coupling force and the differential velocity between coupling plates 609 and 610. Alternately, an electronically controlled variable damping element may be used in series with force sensor 617 between mounts 609 and 610, to provide an arbitrary non-linear dissipative coupling.

Utilizing a nonlinear dissipative coupling between pairs of elements in a multiple-parallel-element spring allows joint spring rates in a prosthetic limb which are a function of velocity. Thus, a joint spring rate can automatically become stiffer when running than it is while walking.

In one preferred embodiment, chamber 615 is rigidly mounted to mount 610. In another preferred embodiment, chamber 615 is mounted to mount 610 through coupling spring 623. In a preferred embodiment, coupling spring 623 may be an actively-controlled variable stiffness spring according to the present invention.

Figure 13:
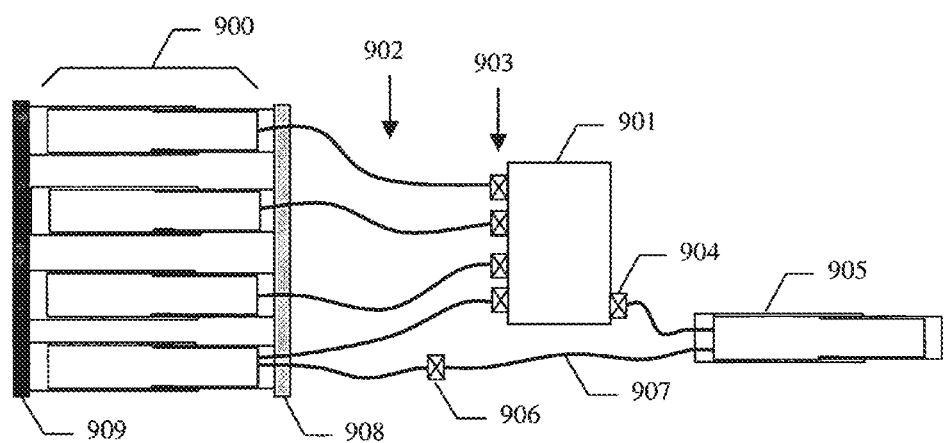
FIG. 13: Multiple-pneumatic-chamber variable spring rate and energy transfer system.

FIG. 13 depicts a multiple-couplable-parallel element pneumatic embodiment of the present invention. Multiple parallel pneumatic chambers 900 couple mounting plates 908 and 909. Pneumatic hoses 902 connect chambers 900 to a common chamber 901 through individually actuatable valves 903. Spring stiffness between plates 908 and 909 is maximized when all valves 903 are closed, and minimized when all valves 903 are open. Additional pneumatic element 905 may be added to transfer power from one prosthetic joint to another.

In an immediate-energy-transfer embodiment of the present invention according to FIG. 13, valves 904 and 906 may be timed to actuate in sequence with valves 903 to transfer power directly from chamber 905 to chambers 900. In a delayed-energy-transfer embodiment of the present invention according to FIG. 13, energy may be transferred from chamber 905 to chambers 900 or vice versa in a delayed manner, by chambers 900 or chamber 905 first pressurizing chamber 901, then isolating chamber 901 by closing valves 903 and 904 for some period of time, then transferring the energy stored in chamber 901 to chambers 900 or 905 by opening the appropriate valves.

Figure 15:
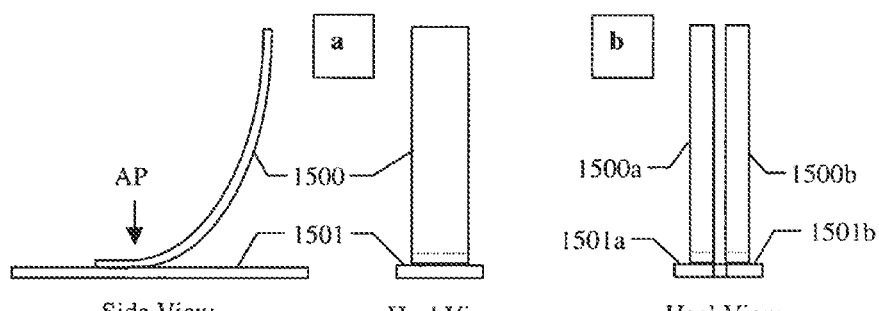
FIG. 15: Example prosthetic ankle/foot known in the art.

FIG. 15a depicts a prosthetic ankle-foot system known in the art. Ankle spring 1500 is affixed to foot-plate 1501. One variable-stiffness embodiment of the present invention shown in FIG. 15 uses a multiple-parallelly-interlockable-leaf-spring structure such as that shown in FIG. 12 in place of ankle spring 1500. Multiple-parallelly-interlockable-leaf-spring 1600 allows for different spring rates in forward and backward bending, allowing separately controllable rates of controlled plantar-flexion and controlled dorsi-flexion.

Figure 14:
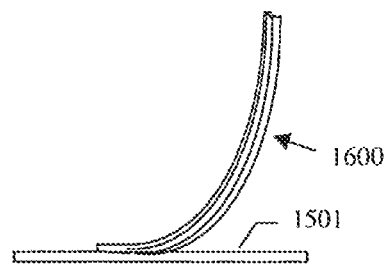
FIG. 14: Prosthetic ankle/foot utilizing multiple interlockable parallel leaf springs for ankle spring.

In one embodiment of the present invention (shown in FIG. 15b), ankle spring 1500 is split into inner ankle spring 1500a, and outer ankle spring 1500b, and heel spring 1501 is split rearward of attachment point AP into inner heel spring 1501a and outer heel spring 1501b. In a preferred embodiment, ankle springs 1500a and 1500b and heel springs 1501a and 1501b each comprise actively-variable multi-leaf springs such as ankle spring 1600 in FIG. 14. Having separate inner and outer variable-stiffness ankle springs allows for active control of side-to-side stiffness of the prosthetic ankle joint. Having separate inner and outer variable-stiffness heel springs allows for active control medio-lateral ankle stiffness.

Figure 16:
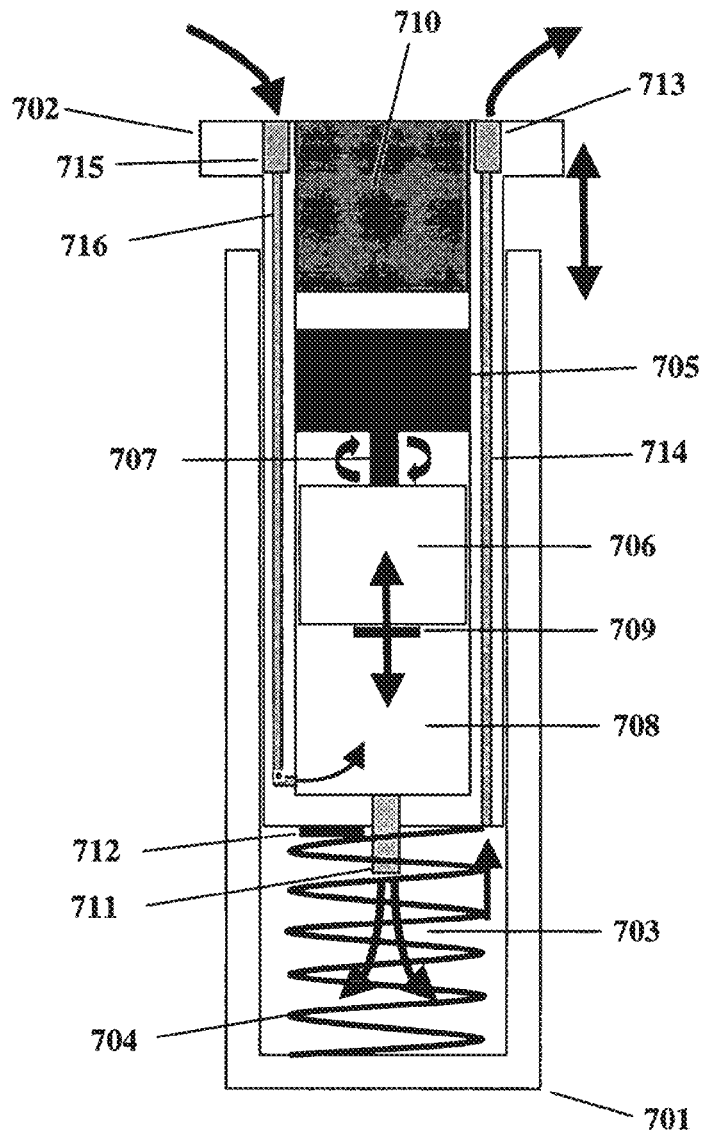
FIG. 16: Variable-stiffness pneumatic spring.

A pneumatic embodiment of a variable-stiffness spring for a prosthesis is shown in FIG. 16. Male segment 702 comprises one end of the overall variable-stiffness spring, and female segment 701 comprises the other end. Control electronics 710 are contained in the upper end of male segment 710. Intake valve 715 is actuatable to allow air to enter pressure chamber 708 through air intake channel 716 when pressure chamber 708 is below atmospheric pressure (or an external pump may be used to allow air to enter even when chamber 708 is above atmospheric pressure). Air pressure sensor 709 senses the pressure in pressure chamber 708. Pressure chamber 708 is coupled to second pressure chamber 703 through valve 711. The air in pressure chamber 703 acts as a pneumatic spring in parallel with spring 704. Motor 705 turns ball screw 707 to move piston 706 back and forth to control the volume of pressure chamber 708. Pressure in pressure chamber 703 may be lowered to a desired value by opening valve 703 for a controlled period of time, allowing air to escape through pressure release channel 714.

In one mode of operation, valve 711 is open and pressure chambers 708 and 703 combine to form a single pressure chamber. In this mode, movement of piston 706 directly controls the overall pressure chamber volume, and thus the overall pneumatic spring rate. In another mode of operation, valve 711 is closed, and valve 706 may be opened and piston 706 may withdrawn to add air to the system.

In a preferred embodiment of a variable-stiffness leg prosthesis according to the present invention is implemented through the pneumatic system of FIG. 16, motion of piston 706 occurs under minimal load, such as during the phase of gait when the foot is off the ground, or when the user is standing still.

The pneumatic system shown in FIG. 16 may also be used to implement immediate-release or delayed-release catapult embodiments of the present invention. An immediate-release catapult may be implemented by opening valve 711, and using motor 705 to add power (for instance, during the powered plantar-flexion phase of gait) as the power is needed. In a delayed-release catapult embodiment of the present invention, valves 715 and 711 are closed while motor 705 moves piston 706 to pressurize chamber 708, and then energy stored in chamber 708 is rapidly released during a phase of gait to produce the same effect as powered plantar-flexion.

In a preferred embodiment of the present invention, a pneumatic prosthetic leg element according to FIG. 16 is combined with the multiple controllably-couplable parallel leaf spring prosthetic ankle-foot of FIG. 15 to provide a prosthetic limb which provides powered plantar-flexion, controllable compressional leg spring stiffness, and controllable ankle stiffness during controlled plantar-flexion and controlled dorsi-flexion.

CLAIMS

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

Having described the invention, what is claimed is:

1. A biarticular prosthetic or orthotic leg comprising:
   a support member connected at its upper end to an above-knee segment, said support member configured to rotate with respect to said above-knee segment to define a knee joint;
   a foot member including a rearwardly extending heel portion and a forwardly, extending toe portion to make periodic bearing contact with ground, said foot member operably connected to a lower end of said support member and configured to rotate relative to said support member to define an ankle joint;
   an anterior spring connected to the above-knee segment and to the support member, the anterior spring displaced from the knee joint and configured to store energy when said support member rotates about said knee joint to move said foot member rearwardly with respect to said above-knee segment and configured to release energy to rotate said support member about said knee joint;
   a biarticular posterior spring connected to the above-knee segment and to the heel portion of the foot member, the posterior spring displaced from the knee joint and configured to store energy when said support member is rotated in an extension movement about said knee joint and configured to release energy to rotate said foot member about said ankle joint to increase bearing force applied to the ground by said toe portion during powered ankle plantarflexion and to impart lifting force against the ground; and
   an anterior clutch connected in series with the anterior spring, the anterior clutch to engage the anterior spring at select engagement times when said support member rotates about said knee joint.

2. The prosthetic or orthotic leg of claim 1, the anterior spring to store energy when said support member rotates about said knee joint to move said foot member rearwardly with respect to said knee joint during an early stance knee flexion stage of a gait cycle that follows heel-strike when said heel portion of said foot member first contacts the ground and to provide shock absorption.

3. The prosthetic or orthotic legs of claim 2, wherein energy released by the anterior spring is transferred to the posterior spring as said support member rotates about said knee joint during a knee extension movement.

4. The prosthetic or orthotic leg of in claim 1, wherein the posterior spring also is configured to store energy during a dorsi-flexion stage of a gait cycle when said support member rotates forwardly about said ankle joint as said foot member remains in contact with the ground.

5. The prosthetic or orthotic leg of claim 4, wherein energy released by the anterior spring is transferred to the posterior spring as said support member rotates about said knee joint during a knee extension movement.

6. The prosthetic or orthotic leg of claim 1, wherein the posterior spring is connected in series with at least one controllable clutch and is configured to store and release energy as said foot member rotates about said ankle joint.

7. The prosthetic or orthotic leg of claim 1, wherein energy released by the anterior spring is transferred to the posterior spring at a predetermined time during a gait cycle.

8. The prosthetic or orthotic leg of claim 1, wherein energy released by the anterior spring is transferred to the posterior spring while said support member rotates about said knee joint in a knee extension movement.

9. The prosthetic or orthotic leg of claim 1, wherein the posterior spring is configured to release energy during a powered plantar-flexion stage of a gait cycle when the said toe portion of said foot member presses against the ground and raises said heel portion from the ground delivering power to the walking step.

10. The prosthetic or orthotic leg of claim 1, wherein the posterior spring is connected in series with at least one controllable clutch and is configured to store and release energy as said foot member rotates about said ankle joint.

11. The prosthetic or orthotic leg of claim 1, wherein the posterior spring is connected in series with at least one controllable clutch and is configured to store and release energy as said foot member rotates about said ankle joint.

12. The prosthetic or orthotic leg of claim 1, wherein the anterior spring and the posterior spring are configured to store and release energy under the control of one or more clutches.

13. The prosthetic or orthotic leg of claim 1, wherein the anterior spring and the posterior spring are pneumatic springs configured to store and release energy via a fluid transfer system controlled by one or more controllable valves.

14. A prosthetic or orthotic leg comprising:
   an above-knee segment configured to attach to a biological limb of a human body above a knee of the human body;
   a support member attached at its upper end to the above-knee segment and configured to rotate with respect to the above-knee segment to define a knee joint;
   a foot member attached to a lower end of the support member and configured to rotate with respect to the support member to define an ankle joint, the foot member making periodic bearing contact with ground during a walking, running or jumping gait cycle, the foot member including a toe portion at its forward end and a heel portion at its rear end;
   a biarticular spring connected to the above-knee segment and to the foot member, the biarticular spring displaced from the knee joint and operationally coupled past the knee joint and configured to store energy when the knee joint extends and the ankle dorsi-flexes during a stance phase of walking, the biarticular spring being further operationally coupled past the ankle joint and configured to release energy used to rotate the foot member about the ankle joint in order to increase bearing force applied to the ground by the toe portion during powered ankle plantar-flexion and to impart lifting force against the ground; and one or more clutches operably coupled to the biarticular spring, the one or more clutches configured to control the store and release of said energy.

15. A prosthetic or orthotic leg of claim 14, wherein the biarticular spring is operationally coupled past both the knee joint and the ankle joint during controlled ankle dorsiflexion in the stance phase of walking and configured to store energy due to both knee extension and ankle dorsi-flexion.

16. A prosthetic or orthotic leg of claim 15, wherein the biarticular spring is operationally coupled to the ankle joint but operationally decoupled from the knee joint during ankle plantarflexion.

17. A prosthetic or orthotic leg of claim 14, further comprising an additional spring pivotably connected between the above-knee segment and the support member, the additional spring being displaced from the knee joint rotational axis and operationally coupled past the knee joint and configured to store energy as the knee flexes during early stance knee flexion and configured to release energy as the knee extends.

18. A prosthetic or orthotic leg of claim 17, wherein the biarticular spring and the additional spring are configured to store and release energy under the control of the one or more clutches.

19. A prosthetic or orthotic leg of claim 17, wherein at least one of the biarticular spring and the additional spring are pneumatic springs configured to store and release energy via a fluid transfer system controlled by one or more controllable valves.

* * * * *